(12) United States Patent
Lippitt et al.

(10) Patent No.: US 10,117,661 B2
(45) Date of Patent: Nov. 6, 2018

(54) STONE EXTRACTING MEDICAL DEVICE WITH BETTER STONE RETENTION

(71) Applicant: Cook Medical Technologies LLC, Bloomington, IN (US)

(72) Inventors: Robert G. Lippitt, Smithfield, NC (US); Raymond F. Lippitt, Smithfield, NC (US)

(73) Assignee: Cook Medical Technologies LLC, Bloomington, IN (US)

( * ) Notice: Subject to any disclaimer, the term of this patent is extended or adjusted under 35 U.S.C. 154(b) by 226 days.

(21) Appl. No.: 14/717,295

(22) Filed: May 20, 2015

(65) Prior Publication Data

US 2015/0342624 A1    Dec. 3, 2015

Related U.S. Application Data

(60) Provisional application No. 62/005,591, filed on May 30, 2014.

(51) Int. Cl.
   *A61B 17/221* (2006.01)
(52) U.S. Cl.
   CPC .... *A61B 17/221* (2013.01); *A61B 2017/2215* (2013.01); *A61B 2017/2217* (2013.01)
(58) Field of Classification Search
   CPC . A61B 17/221; A61B 17/32056; A61B 17/26; A61B 2017/2215; A61B 2017/2217; A61B 2017/2212
   See application file for complete search history.

(56) References Cited

U.S. PATENT DOCUMENTS

| | | | |
|---|---|---|---|
| 1,723,091 | A | 8/1929 | St. John |
| 2,549,257 | A | 4/1951 | Staunt |
| 2,990,668 | A | 7/1961 | Brendel |
| 3,472,230 | A | 10/1969 | Fogarty |
| 3,481,641 | A | 12/1969 | Berger et al. |
| 4,046,150 | A | 9/1977 | Schwartz et al. |
| 4,198,960 | A | 4/1980 | Utsugi |
| 4,254,979 | A | 3/1981 | Bau |
| 4,347,846 | A | 9/1982 | Dormia |

(Continued)

FOREIGN PATENT DOCUMENTS

| | | |
|---|---|---|
| DE | 29 45 237 | 5/1981 |
| DE | 37 17 657 | 12/1998 |

(Continued)

OTHER PUBLICATIONS

Extended European Search Report for EP 15 16 9489, dated Jul. 7, 2015, 6 pp.

(Continued)

*Primary Examiner* — Anh Dang
(74) *Attorney, Agent, or Firm* — Brinks Gilson & Lione

(57) ABSTRACT

A medical device comprising a cannula having a stone extracting unit on its distal end and a hand piece on its proximal end for operating the unit through the cannula. The unit includes more than four annularly arranged tubular elements with fixed proximal ends and distal ends movable between opened and closed position by the movement of an equal number of wire elements extending through the tubular elements with their distal free ends fixed to the distal ends of tubular elements so as to define a 5 or 6 pointed star configuration.

14 Claims, 6 Drawing Sheets

(56) References Cited

U.S. PATENT DOCUMENTS

| | | |
|---|---|---|
| 4,471,777 A | 9/1984 | McCorkle, Jr. |
| 4,611,594 A | 9/1986 | Grayhack et al. |
| 4,655,219 A | 4/1987 | Petruzzi |
| 4,807,626 A | 2/1989 | McGrirr |
| 4,997,435 A | 3/1991 | Demeter |
| 5,108,406 A | 4/1992 | Wagi |
| 5,190,557 A | 3/1993 | Borodulin |
| 5,193,533 A | 3/1993 | Body |
| 5,312,417 A | 5/1994 | Wilk |
| 5,376,094 A | 12/1994 | Kline |
| 5,417,697 A | 5/1995 | Wilk et al. |
| 5,454,365 A | 10/1995 | Bonutti |
| 5,496,330 A | 3/1996 | Bates et al. |
| 5,522,819 A | 6/1996 | Graves et al. |
| 5,613,973 A | 3/1997 | Jackson et al. |
| 5,735,847 A | 4/1998 | Gough et al. |
| 5,814,052 A | 9/1998 | Nakao |
| 5,906,622 A | 5/1999 | Lippitt et al. |
| 5,924,175 A | 7/1999 | Lippitt et al. |
| 5,968,064 A | 10/1999 | Selmon et al. |
| 6,077,274 A | 6/2000 | Ouchi et al. |
| 6,368,327 B2 | 4/2002 | Lippitt et al. |
| 6,743,228 B2 | 6/2004 | Lee |
| 7,041,108 B2 | 5/2006 | Lippitt et al. |
| 7,210,210 B2 | 5/2007 | Lippitt et al. |
| 2003/0225419 A1 | 12/2003 | Lippitt et al. |
| 2011/0264106 A1* | 10/2011 | Taube ............ A61B 17/22031 606/113 |

FOREIGN PATENT DOCUMENTS

| | | |
|---|---|---|
| EP | 0695534 A2 | 2/1996 |
| EP | 0 769 305 | 4/1997 |
| WO | WO 94 06357 | 3/1994 |
| WO | WO 1996010961 | 4/1996 |
| WO | WO 01/80748 A2 | 11/2001 |
| WO | WO 2005/034774 A1 | 4/2005 |
| WO | WO 2014/002087 A1 | 1/2014 |

OTHER PUBLICATIONS

NGage® Nitinol Stone Extractor, Cook Medical Brochure, Cook 2013, 2 pp.

* cited by examiner

STONE EXTRACTING MEDICAL DEVICE WITH BETTER STONE RETENTION

This application claims priority from U.S. Provisional Application No. 62/005,591, filed on May 30, 2014, the entirety of which is hereby fully incorporated by reference herein.

FIELD OF THE INVENTION

This invention relates to medical devices and more particularly to such stone extracting medical devices. Such device typically includes a stone extracting unit which is mounted on one end of an elongated cannula and is capable of being operated in response to the movement of a hand piece mounted on the other end of the cannula.

BACKGROUND OF THE INVENTION

The invention constitutes an improvement on the medical stone extracting device disclosed in U.S. Pat. No. 5,906,622, which is manufactured in accordance with U.S. Pat. No. 7,210,210 and sold commercially under the trade mark "N-Gage" by Cook Urological. The disclosure of the '622 and '210 patents are hereby incorporated by reference into the present specification. The "N-Gage" device includes a stone extracting unit mounted on the distal end of an elongated cannula operated by a hand piece mounted on the proximal end of the cannula. The stone extracting unit itself comprises three annularly arranged elongated tubular elements fixed together at their proximal ends to a distal end of a fixed component of the cannula, the proximal end of which is connected to a fixed component of the hand piece. The manually movable component of the hand piece is connected to the proximal end of a movable component of the cannula which extends through the fixed component of the cannula. The distal end of the movable cannula component is connected to move three elongated wire elements of the stone extracting unit. The three elongated wire elements extend through the three fixed tubular elements so that their free end portions extend outwardly of the free ends of the tubular elements. The free ends of the three wire elements are then connected in fixed relation to the exterior free end portion of an adjacent tubular element by the method disclosed in the aforesaid '210 patent. The arrangement is such that when the movable component of the hand piece is manually moved from a closed position to an opened position, the free ends of the tubular elements of the stone extracting unit are moved radially outwardly with respect to one another by virtue of the wire elements moving outwardly of the free ends of the tubular elements while their free ends are connected to free ends of adjacent tubular elements.

An advantage of the "N-Gage" device is that it can be used to capture stones (1) in the kidney, in which case entry of the stone is through the open center defined by the wire elements backed up by the diverging tubular elements or (2) in the ureter, in which case entry of the stone is between spaced apart backup tubular elements.

BRIEF DESCRIPTION OF THE INVENTION

The improvement of the present invention is particularly suited for use in applications involving larger spaces than the ureter because, with a larger radial expansion of the tubular elements, the distance between adjacent backup portions of the tubular elements becomes greater. In the renal environment this distance can be great enough to make maintaining capture of the stone problematic. In accordance with the principles of the present invention, the solution is to provide more backup tubular elements to reduce the distance between adjacent tubular elements when the device is wide open. In particular Nephrostolithotomy procedures where the variety of stone sizes that need and can be extracted is significantly larger than in other applications such as Pyelonetroscopic approaches. The present invention is particularly useful in procedures which present these circumstances.

Applicants have found that while the four wire device disclosed in the '622 patent does work, it does not have to necessarily work all the time.

As discussed in the '622 patent, the tubes and wires of a four element device when closed and viewed from the end form a four pointed star. The four points of this star are defined by the ends of the tubular elements. The sides leading to each point are defined by the two wire elements extending angularly to the end of each tubular element. In a four element device the wire elements must extend from the end of a tubular element to an adjacent tubular element. The only other possibility is the wire element extends to a diametrically opposite one, and this cannot be done because it would close the necessary open end. The angle between each pair of wire elements leading to a point at a tubular element end is 90°.

The opening movement of a device in its closed position is the most difficult movement to accomplish because of the very little leverage available for the wire elements to move the ends of the tubular elements radially outwardly from their abutting annular configuration. If all four are moved radially out together, the device opens up normally. Applicants have found that sometimes at the beginning, one point of the four will start moving inwardly toward the opposite point because the 90° angle of the wire elements allows this to take place and to continue. The small triangle of the inwardly moving point essentially inverts and continues to move in inverted relation toward the opposite point resulting in an opening malfunction where the required open center is closed by wire elements extending therein.

In constructions where the device is made up of more than four elements and the wire elements are connected to adjacent tubular element ends as taught in the '622 patent, the same triangularity would exist throughout the annulus but with an angle greater than 90° with the respect to each triangle which could, in operation, invert to cause an opening malfunction.

Applicants have found that multiple element devices involving more than four elements can be made so that the inverion and opening malfunction mentioned above does not occur so long as the wire elements are connected to the end of a tubular element which is neither adjacent to nor diametrically opposed to the tubular element from which it extends. In a five element device constructed in accordance with the principles of the present invention, the end view of the closed device is in the shape of a five pointed star that can be drawn by not removing a pen from the paper on which the star is drawn. The comparable configuration of a six element device according to the invention is in the shape of a six pointed star made up of two deltas drawn on the same center but equally angularly displaced with respect to one another. Devices having more than six elements are contemplated within the invention.

Other objects, features, and advantages of the present invention will become apparent from the following detailed description, the accompanying drawings, and the appended claims.

DETAILED DESCRIPTION OF THE PREFERRED EMBODIMENTS OF THE INVENTION

Figure 1:
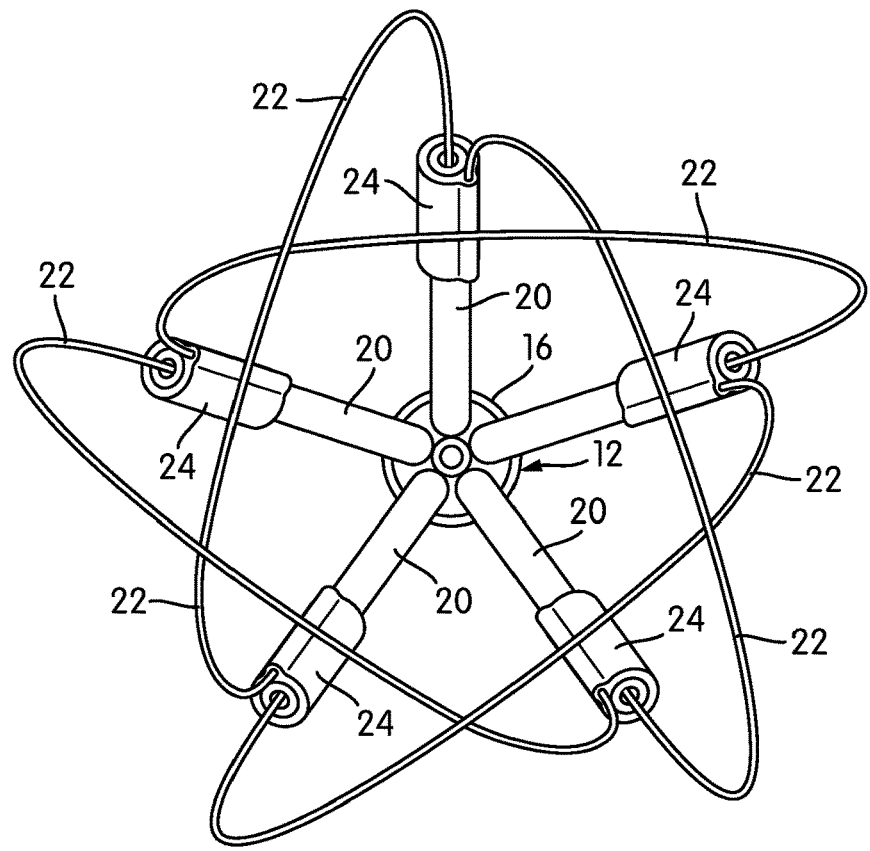
FIG. 1 is a top plan view of a medical device embodying the principles of the present invention showing the five cooperating elements of the stone extracting unit in an open position.

Referring now particularly to FIGS. 1-7 of the drawings, there is shown therein one embodiment of a medical device, generally indicated at 10, which embodies the principles of the present invention. The medical device 10 includes, in general, an elongated cannula assembly, generally indicated at 12, a hand piece assembly, generally indicated at 13, operatively connected with the proximal end portion of the cannula assembly 12, and a stone extracting unit 14 operatively connected to the distal end of the cannula assembly 12.

In the embodiment shown in FIGS. 1-8, the cannula assembly 12 is formed of a fixed outer tubular component 16 and a movable inner tubular component 18. However the construction can be made in accordance with the constructions disclosed in either of the aforesaid patents.

The tubular elements 16 and 18 are formed of a suitable plastic material such as polyethylene, polypropylene, polyester, polyvinyl chloride, polyimide or the like.

At the distal end of the cannula assembly 12, the fixed outer tubular component 16 extends over and is fixed to the proximal ends of five annularly arranged abutting tubular elements 20 (constituting longitudinally fixed flexure elements as described in the '622 patent) forming a part of the stone extracting unit 14 at the distal end of the cannula assembly 12.

The stone extracting unit 14 also includes five wire elements 22 (constituting movable flexure elements as described in the '622 patent) which extend through the five tubular elements 20. The proximal ends of the five wire elements 22 are connected with the distal end of the movable inner cannula element 18 within the fixed outer cannula element inwardly of the associated proximal ends of the tubular elements 20. The wire elements 22 are preferably made of nitinol and the tubular elements are made of a suitable plastic material as, for example, a mixture of ethylene vinyl acetate and low density polyethylene.

Figure 2:
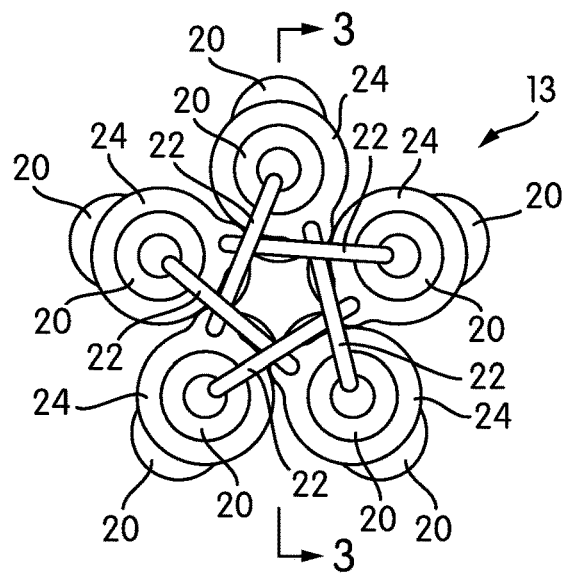
FIG. 2 is an enlarged end view of the device shown in FIG. 1 with the five elements of the stone extracting unit in a closed position around a stone.

The five wire elements 22 extend outwardly from their respective surrounding tubular elements 20 and their distal ends are connected with the distal ends of the tubular elements 20 so that, as shown in FIG. 2, the exposed portions of the wire elements 22 when drawn into a closed position define a five pointed star continuously drawn without interruption. In accordance with the principles of the present invention it is important to note that the free end of each wire element 22 has its distal free end connected to the end of a tubular element 20 which is neither adjacent to nor diametrically opposed to the tubular element 20 from which the wire element 22 extends. It will also be noted that there are two wire elements 22 associated with the end of each tubular element 20, one moveably extending therefrom and one fixed thereto.

The two wire elements 22 associated with each tubular element extend therefrom in a V-formation where they are associated with the ends of two spaced tubular elements 20. When the wire elements 22 are moved relative to the ends of the tubular elements, the forces are applied in a direction so that they act toward the point of the V which cannot have relative annular movement and toward the free ends of the V which can have annular movement, thus assuring that the movement of the wire elements 22 will have the desired effect of either opening or closing the distal end of the unit 14.

It will also be noted that when the wire elements 22 are extended to a fully opened position, the exposed portion of each wire element 22 interengages with the exposed portions of two other wire elements 22. As shown, these interengagements are made to go over and under in a consistent pattern which also aids in causing the exposed portions of the wire elements to move in the desired way.

It is preferable that the distal free end of each wire element 22 be connected in fixed relation to the distal end of its associated tubular element 20 by the process and construction disclosed in the patent, although other constructions may be used briefly. The patent process involves positioning a heat shrinkable plastic tube over a heat fusable plastic tube, positioning both tubes over the end portion of the tubular element 20. The distal end portion of the wire element 22 is then inserted between the exterior of the tubular element 20 and the interior of the inner fusable plastic tube. Heat is then applied to the heat shrinkable tube which moves radially inwardly heating the fusable plastic of the inner tube which acts as an adhesive to ensure that the heat shrunk tube holds the wire end in glued engagement with the exterior of the end of the tubular element 20. In the drawings, the fused together outer heat shrinkable plastic tube and the inner fusable plastic tube are shown as one unit and identified by the reference numeral 24.

The connection between the proximal ends of the wire elements 22 and the distal end of the inner movable cannula element 18 may assume any of the configurations shown in the aforesaid patents. The connection shown in FIG. 3 includes a solid cylindrical pusher member 28 having five equally spaced wire receiving grooves 30 formed in the exterior periphery thereof. The proximal end portion of each wire element 22 is kinked at a right angle, as indicated at 32, and the portion inwardly thereof is mounted in a groove 30 so that the kinked end 32 engages the proximally facing surface of the pusher member 30. An annular retaining member 34 of angular cross-section is fitted over the wire containing pusher member 28 is engagement with the kinked end 32.

The center of the pusher member 28 is drilled and threaded to receive a thread bolt 36 therethrough. The bolt 36 extends outwardly a considerable distance from the pusher member 28 so as to be useful in mounting the annular retaining member 34 in its fitted position. Proximally threadedly mounted on the extending end portion of the bolt 36 is a cannula connecting member 38 having a distally facing surface which, when the member 38 is tightened onto the bolt 36, engages and wedges the retaining member 34 in its fitted position.

The exterior periphery of the cannula connecting member 38 is formed with three different configurations including wrench engaging flats 40 adjacent the distally facing surface thereof, a section of threads 42 in the middle portion and a frusto-conical surface 44 at the proximal end thereof.

Figure 3:
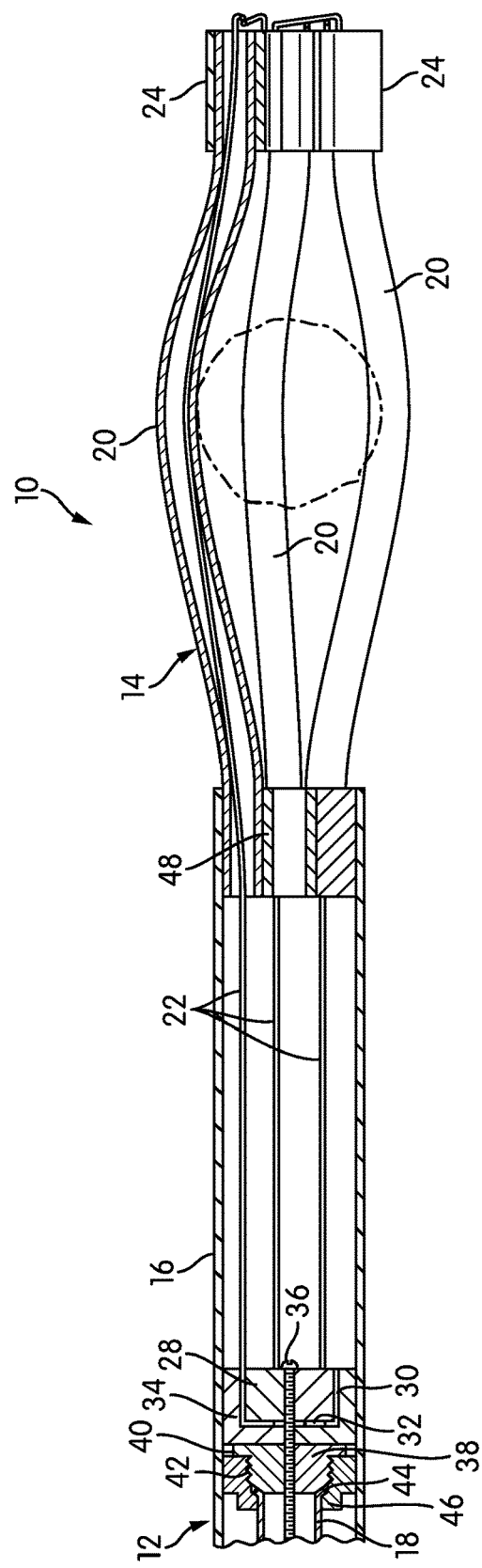
FIG. 3 is a reduced cross-sectional view taken along the line 3-3 of FIG. 2.

As can be seen in FIG. 3, the movable inner cannula component 18 has its distal end split so as to engage over and seat on the frusto-conical surface 44. The distal end of movable inner cannula component 18 is secured to the cannula connecting member 38 with its split end in wedged engagement with the frusto-conical surface 44 by a mating frusto-conical surface of an annular retaining member 46 threaded on the threaded section 42 of the cannula connecting member 38.

The two retaining members 34 and 46 have their cylindrical exterior peripheries sized so as to easily slide within the interior cylindrical periphery of the fixed outer cannula component 16.

The assembly of the five wire elements 22 with the five tubular elements 20 and the movable inner cannula component can be accomplished in any suitable fashion. One manner of assembly is to first secure the distal ends of each wire element to the end of its associated tubular element 20 by the method previously described. The proximal ends of the tubular elements 20 are then secured together by gluing them around a short tube 48. With the tubular element 20 thus initially secured together, the appropriate wire elements 22 can be fed through the tubular elements 20 until the proximal ends extend proximally beyond the proximal ends of the tubular elements 20.

The portions of the wire elements 22 are then kinked and fitted on the pusher member 28 and the retaining member 34 is then pushed into fitted relation thereto.

The cannula connecting member 38 can now be threaded onto the bolt 36 and cinched down by using a wrench on the flats 40 while holding the retaining member 34 in fitted relation to the pusher member 28. Then, after slipping the retaining ring 46 over the inner movable cannula element 18, the distal end of the inner movable cannula component 18 is split and engaged with the frusto-conical surface 44. The retaining ring 46 can then be moved along the cannula component 18 and threaded on the threaded section 42 to complete the connection between the cannula component 18 and the five wire elements 22. The connection of the cannula assembly 12 with the stone extracting unit 14 is completed by moving the fixed outer cannula component 20 into position with its distal end portion over the proximal ends of tubular elements 20 held in position by the tube 48 and glued in place.

Referring now more particularly to FIGS. 4-7, the construction of the hand piece assembly 13 and its connection with the proximal end of the cannula assembly 12 will now be described. The hand piece assembly 13 constitutes a moving mechanism for the stone extracting unit 14 which operates through the cannula assembly. It will be understood that other types of moving mechanisms are contemplated.

Figure 4:
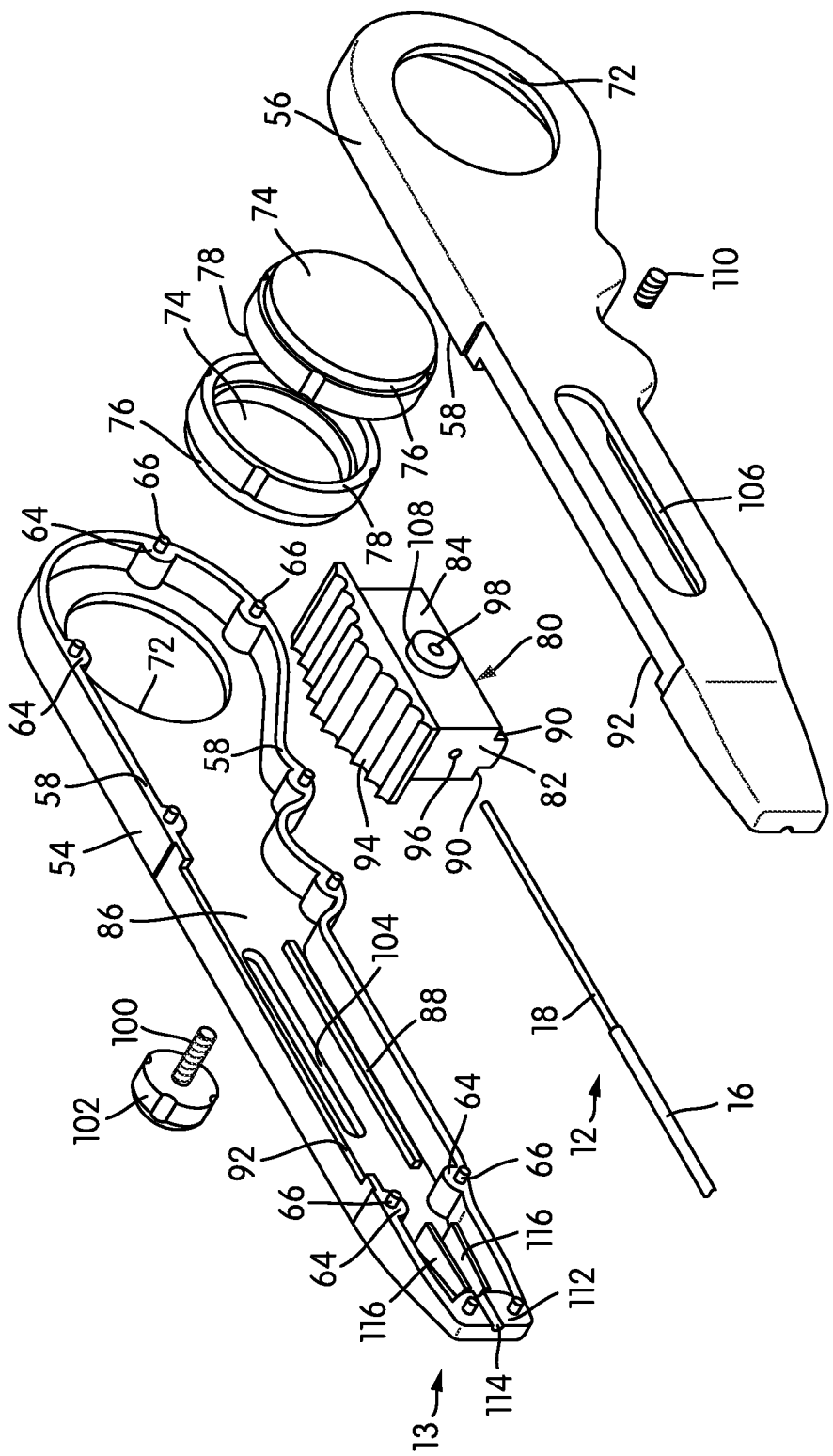
FIG. 4 is an exploded perspective view of a typical hand piece which can be used in the 5 element device shown in FIG. 1 as well as the 6 element device shown in FIGS. 8-10.

The hand piece assembly 13 may assume any known configuration. However, as shown, the hand piece assembly 13 is a known assembly manufactured and commercially sold by CR Bard, Inc. As best shown in FIG. 4, the moving hand piece assembly 13 includes a fixed housing component or assembly, generally indicated at 50, and a moving component or assembly, generally indicated at 52, slidably mounted in the fixed housing assembly 50 between limiting positions, one of which corresponds to the closed position of the stone extracting unit 14 and the other of which corresponds to the open position of the stone extracting unit 14.

The fixed housing assembly 50 includes two complimentary split housing members 54 and 56, best shown in FIG. 4, molded of a suitable plastic material, such as ABS or polycarbonate. The housing members 54 and 56 are of shell-like construction, with edges 58 configured to be moved into complementary abutting relation with one another so as to form a three dimensional gun-like shape including a rear handle portion 60 configured to be gripped by one hand of a user and a barrel portion 62 extending forwardly therefrom from which the cannula assembly 12 extends.

Figure 5:
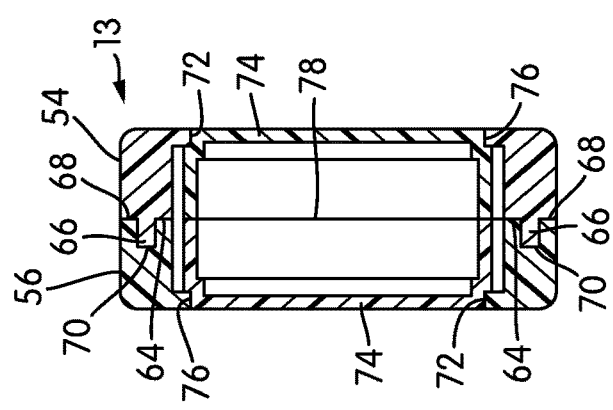
FIG. 5 is a cross-sectional view of the hand piece shown in FIG. 4 assembled with the cannula taken along the outer end portion thereof.

The housing member 54 includes a series of peripherally spaced bosses 64, each having a projection 66 extending from the central portion thereof. As best shown in FIG. 5, the housing member 56 includes a series of abutting bosses 68, each having a central opening 70 therein sized to receive a corresponding projection 66. The handle portions of the housing members 54 and 56 have large circular openings 72 therein each sized to receive therein a logo carrying circular member 74. The circular members 74 are of generally cup-like configuration each being peripherally recessed, as indicated at 76, to fit with an associated opening 72 and having circular edges 78 positioned to abut one another.

The moving assembly 52 includes a pusher member, generally indicated at 80, molded of a suitable plastic material, such as ABS or polycarbonate. The pusher member 80 includes a rectangular body portion 82 having a width defined by planar exterior surfaces 84 configured to slidably engage complementary centrally located planar interior surfaces 86 provided by the housing members 54 and 56.

Formed in the lower central portion of each housing member 54 and 56 below the associated planar surface 86 is a rail portion 88 positioned to be slidably engaged by a corresponding rail surface 90 formed along the associated lower corner of the body portion 82 below the associated planar surface 84.

Each housing member 54 and 56 has an elongated recess 92 formed in a central upper portion of the edge 58 thereof. The body portion 82 is suitably recessed along the upper extremities of the planar surfaces 84 to provide an upper section of reduced width which rides within the opening defined by the edges of the recesses 92.

The pusher member 80 also includes an upper thumb engaging portion 94 integral with the body portion 82 along the upper section thereof. The thumb engaging portion 94 extends transversely outwardly beyond the sides of the body portion to provide flange sections which overlie and can slide along the upper exterior surfaces of the housing members 54 and 56 adjacent the recesses 92. As best shown in FIG. 4, the upper surface of the thumb engaging portion 94 is longitudinally convex and formed with spaced ridges to aid thumb manipulation.

The body portion 82 is formed with a longitudinally extending bore 96 sized to receive therein the proximal end of the inner cannula component 18. The body portion 82 also is formed with a transversely extending threaded bore 98 which intersects at its central portion with a central portion of the bore 96.

The portion of the threaded bore 98 on the housing member 54 side of the bore 96 is adapted to receive a threaded stem 100 of a knob 102. The housing member 54 has an elongated slot 104 formed in the central side wall thereof which enables the threaded stem 100 to be threaded into the threaded bore 98 and move with the pusher member 80 while the knob 102 is disposed exteriorly of the fixed housing assembly 50.

The opposite housing member 56 is formed with a comparable parallel slot 106 which has a width dimension larger than the width dimension of the slot 102. The larger width slot 106 is configured to receive therein a circular boss 108 formed integrally on the adjacent planar surface 84 of the pusher member 80. A set screw element 110 is adapted to be threadedly engaged in the portion of the threaded bore 98 on the housing member 56 side of the base 98.

The longitudinal bore 96 together with the threaded stem 100 and set screw element 110 provide the interconnection with the movable component 18 of the cannula assembly 12. After the cannula component 18 is inserted in the bore 96, set screw element 110 can be used to lock the cannula component 18 in the bore 96.

Figure 7:
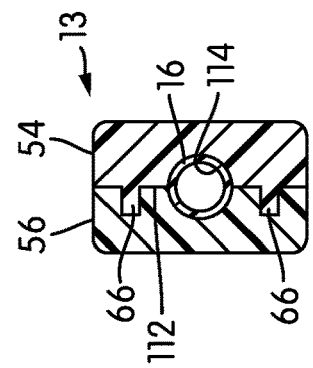
FIG. 7 is a view similar to FIG. 5 taken through the front end portion of the hand piece.
Figure 6:
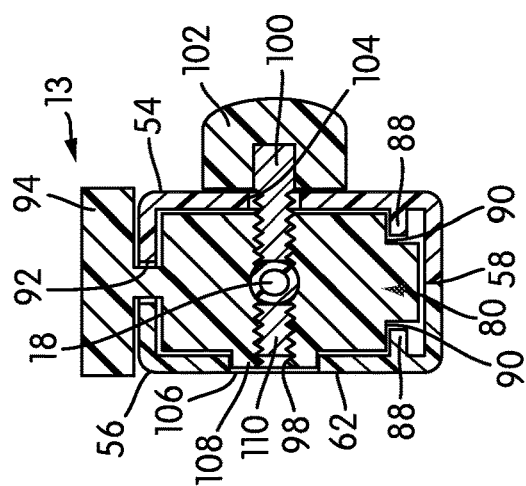
FIG. 6 is a view similar to FIG. 5 taken through the center portion of the hand piece.

The interconnection with the fixed part of the cannula assembly 12 is provided by a large arcuate boss 112, best shown in FIGS. 4 and 7, formed in the forward end of each housing member 54 and 56 having a longitudinal groove 114 of half circle cross section therein. Also, as shown, in FIG. 4, there are two rearwardly extending reinforcing ribs 116 disposed just rearwardly of the arcuate boss 112.

The interconnection is accomplished in conjunction with the assembly of the housing members 54 and 56 together. This assembly, as well as the pre-assembly of the circular members 74 within the circular openings 72, is accomplished by applying an appropriate adhesive to the abutting surfaces of the parts and moving them together. Of course, the pusher member 80 with the attached cannula assembly 12 is properly positioned within the housing members 54 and 56 before they are moved together. During the movement together, the glued surfaces of the grooves 114 engage the exterior surface of the proximal end of the cannula component 16. Additional adhesive can be used between the ribs 116.

Figure 8:
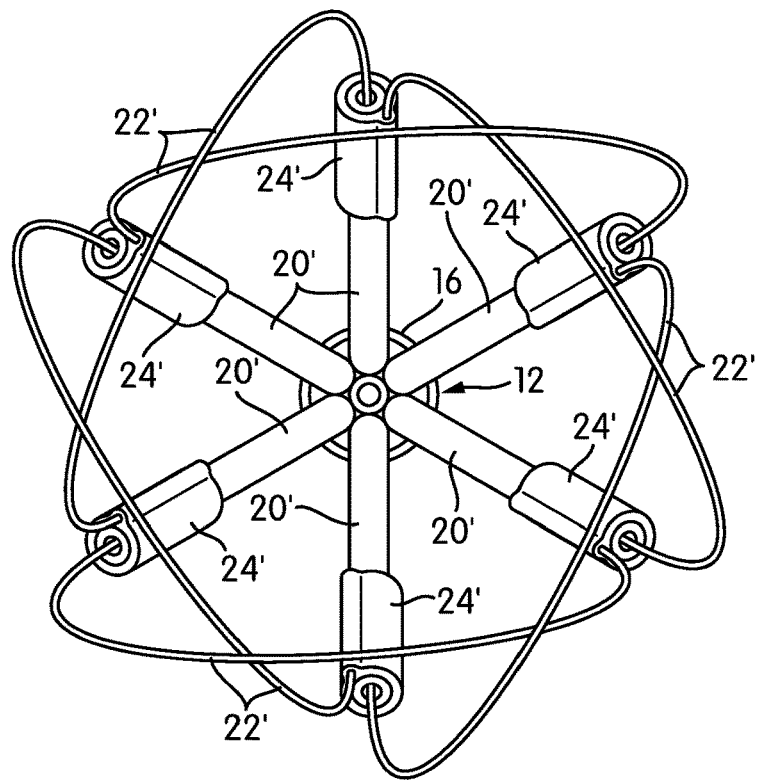
FIG. 8 is a view similar to FIG. 1 showing another embodiment of a medical device of the invention having a six element stone extracting unit.
Figure 9:
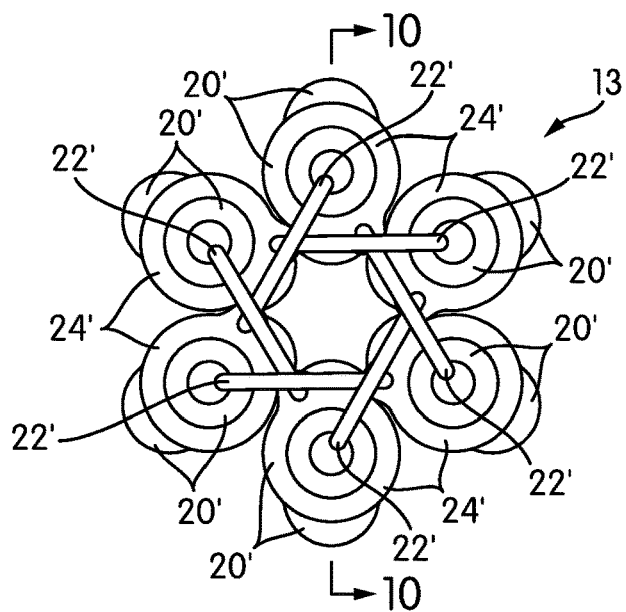
FIG. 9 is a view similar to FIG. 2 of the device shown in FIG. 8.
Figure 10:
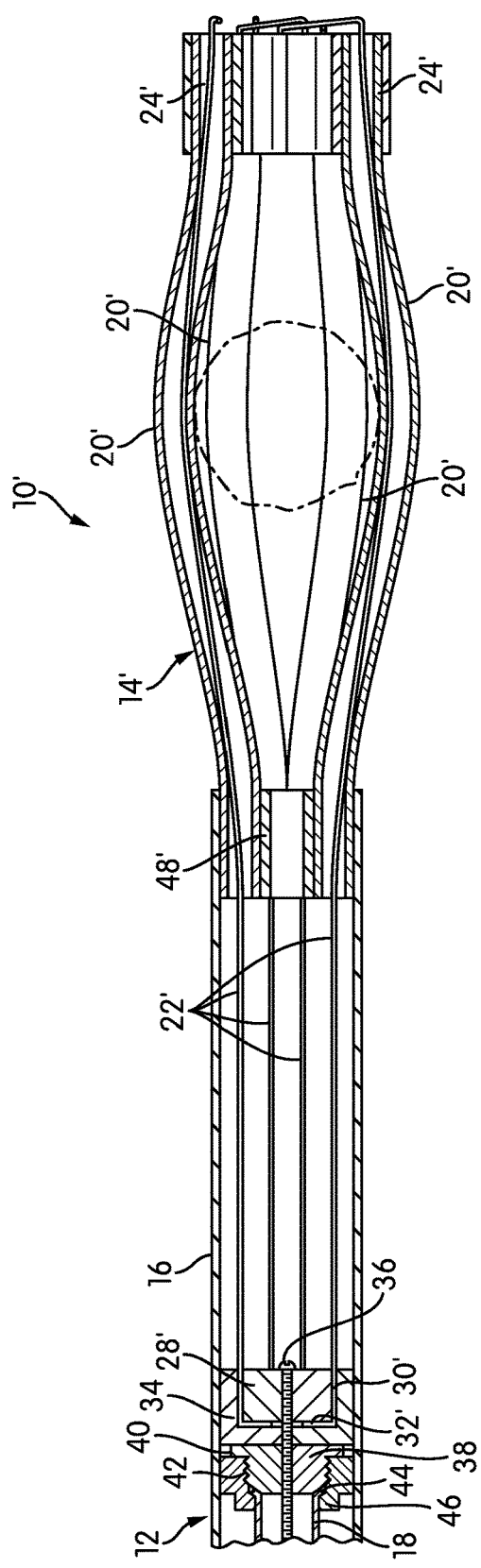
FIG. 10 is a view similar to FIG. 3 of the device shown in FIG. 8.

Referring now more particularly to FIGS. 8-10, there is shown there a six element stone extracting unit 14' which forms another embodiment of the present invention when used in lieu of the 5 element stone extracting unit 14 with the hand piece assembly 13 and cannula assembly 12.

The unit 14' differs from the unit 14 solely in the provision of six cooperating wire and tubular elements rather than five. Consequently, reference numbers used in FIGS. 1-3 to describe the parts of the unit 14 are applied to the comparable parts of the unit 14' in FIGS. 8-10 with a prime (') added thereto. Accordingly, since most of the parts of both units are the same, it is appropriate in describing the unit 14' to describe only the differences that occur by virtue of the provision of six cooperating elements rather than five.

First, it will be noted that the six tubular elements 20' are arranged annularly, like the five tubular elements 20, with their proximal ends fixedly secured together in abutting relation and to the fixed component 16 of the cannula assembly 12 and with their distal ends free to flex outwardly between opened and closed positions. The six wire elements 22' likewise extend through the six tubular elements 20' with their proximal ends fixed to a six groove pusher member replacing the 5 groove pusher member and with their distal end portions extending distally beyond the distal ends of the tubular elements 20.

The connection of the distal ends of the wire 'elements 22' to the distal ends of the tubular elements 20' is the same as before but there is a different pattern formed by the movable wire elements 22' with respect to the tubular elements 20' due to the difference in numbers. In essence, the six wire elements are connected in the same fashion as the two three element device units of the "N-Gage" device, only displaced annularly to intermesh with each other. Stated differently, the pattern is like a six pointed star formed by two deltas drawn on the same center but displaced angularly equidistantly.

With this pattern, the same characteristics of the 5 element unit are retained. That is, each movable wire element 22' is movably associated with respect to one of the tubular elements 20' and fixedly associated with respect to a second tubular element 20' which is neither adjacent nor opposite in the annular arrangement with respect to the one tubular element 20'. Each tubular element 20' is associated with two force-applying wire elements 22' which converge thereto in a V-formation to form a point of a star configuration and ensure radial movement of the point with respect to the annular arrangement in response to the movement of the wire elements 22'. It will also be noted that the distal end portion of each wire element 22' associated with two tubular elements 20 intersects with two other wire element distal portions in an over-and-under relation which aids in insuring a normal opening movement.

The foregoing embodiments have been provided solely for illustrating the structures and functional principles of the present invention, and are not intended to be limiting. To the contrary, the present invention encompasses all modifications, alterations, substitutions, and equivalents with the spirit and scope of the appended claims.

The invention claimed is:

1. A medical device comprising:
    an elongated cannula assembly having a proximal end and a distal end,
    a hand piece assembly connected to the proximal end of the elongated cannula assembly, and
    a stone extracting unit on the distal end of the elongated cannula assembly, the elongated cannula assembly including a fixed cannula component and a movable cannula component movable in opposite directions, with respect to the fixed cannula component,
    the hand piece assembly including a fixed hand piece component connected to a proximal end of the fixed cannula component and a movable hand piece component connected to a proximal end of the movable cannula component to move the movable cannula component in opposite directions in response to the movement of the movable hand piece component in opposite directions with respect to the fixed hand piece component,
    the stone extracting unit including more than four tubular elements having proximal end portions fixed together in an annular arrangement in fixed relation to a distal end of the fixed cannula component and an equal number of wire elements, each wire element of the equal number of wire elements extending through a respective tubular element of the more than four tubular elements, each wire element having a proximal end portion extending proximally beyond the proximal end of the respective tubular element connected to be moved in opposite directions in response to the movement of the movable cannula component in opposite directions, each wire element having a distal end portion extending distally beyond the distal end of the respective tubular element, the distal end portion of each wire element having a free end connected in a fixed relation to a distal end of an associated tubular element of the more than four tubular elements, and the respective tubular element and the associated tubular element being disposed neither adjacent to one another nor diametrically opposed to one another in the annular arrangement thereof so as to cause the distal ends of the respective tubular element and the associated tubular element to move between opened and closed positions in response to the movement of each wire element in opposite directions.

2. A medical device as defined in claim 1 wherein the stone extracting unit includes five tubular elements and when the distal ends of the respective tubular element and the associated tubular element are in the closed position thereof the distal end portions of the wire elements define a five pointed star formed by one continuous line.

3. A medical device as defined in claim 2 wherein the distal end portion of each wire element associated with the respective tubular element and the associated tubular element intersects with the distal end portion of an additional wire element of the equal number of wire elements associated with an additional respective tubular element of the more than four tubular elements and an additional associated tubular element of the more than four tubular elements in an over-and-under relation.

4. A medical device as defined in claim 3 further comprising a heat shrunk tube in surrounding relation to the distal end portion of each wire element and the associated tubular element with an annular layer of fused adhesive plastic between the heat shrunk tube and the distal end of the associated tubular element and the distal end portion of the wire element being in contact with the associated tubular element and the annular layer of fused adhesive plastic.

5. A medical device as defined in claim 4 wherein the proximal end portion of each wire element extends proximally beyond the proximal end of the respective tubular element in a parallel annular array, the proximal end portion of each wire element within a respective groove of annually spaced axially extending grooves formed in a pusher member with the proximal end portion of each wire element kinked at a right angle in engagement with a proximally facing surface of the pusher member.

6. A medical device as defined in claim 1 wherein the distal end portion of each wire element associated with the respective tubular element and the associated tubular element intersects with the distal end portion of an additional wire element of the equal number of wire elements associated with an additional respective tubular element of the more than four tubular elements and an additional associated tubular element of the more than four tubular elements in an over-and-under relation.

7. A medical device as defined in claim 1 further comprising a heat shrunk tube in surrounding relation to the distal end of the associated tubular element with an annular layer of fused adhesive plastic between the heat shrunk tube and the distal end of the associated tubular element and the distal end portion of the wire element being in contact with the associated tubular element and the annular layer of fused adhesive plastic.

8. A medical device as defined in claim 1 wherein the proximal end portion of each wire element extends proximally beyond the proximal end of the respective tubular element in a parallel annular array, the proximal end portion of each wire element being engaged within a respective groove of annually spaced axially extending grooves formed in a pusher member with the proximal end portion of each wire element kinked at a right angle in engagement with a proximally facing surface of the pusher member.

9. A medical device comprising:
an elongated cannula assembly having a proximal end and a distal end,
an operable stone extracting unit on the distal end of the elongated cannula assembly, and
a moving assembly on the proximal end of the elongated cannula assembly constructed and arranged to operate the operable stone extracting unit through the elongated cannula assembly,
the operable stone extracting unit including more than four annularly arranged fixed flexure elements fixed at proximal ends for flexure outwardly therefrom and an equal number of movable flexure elements,
each movable flexure element being movably associated with respect to a respective fixed flexure element of the fixed flexure elements and fixedly associated with respect to an associated fixed flexure element which is neither adjacent nor opposite in the annular arrangement with respect to the respective fixed flexure element, wherein each movable flexure element extends through the respective fixed flexure element and has a distal end portion extending distally beyond a distal end of the respective fixed flexure element, the distal end portion of each movable flexure element having a free end connected in a fixed relation to a distal end of the associated fixed flexure element, and
each fixed flexure element being associated with two force applying movable flexure elements which converge thereto in a V-formation to form a point of a star configuration and ensure radial movement of the point with respect to the annular arrangement in response to the movement of the moveable flexure elements.

10. A medical device as defined in claim 9 wherein the operable stone extracting unit includes five fixed flexure elements and when the fixed flexure elements are in the closed position thereof the distal end portions of the movable flexure elements define a five pointed star formed by one continuous line.

11. A medical device as defined in claim 10 wherein the fixed association of each fixed flexure element with a movable flexure element constitutes a connection comprising a heat shrunk tube in surrounding relation to the distal end of the associated fixed flexure element with an annular layer of fused adhesive plastic between the heat shrunk tube and the distal end of the associated fixed flexure element and the distal end of the associated movable flexure element being in contact with the fixed flexure element and the annular layer of fused adhesive plastic.

12. A medical device as defined in claim 9 wherein the stone extracting unit includes six fixed flexure elements and when the distal ends of the fixed flexure elements are in the closed position thereof the distal end portions of the movable flexure element define a six pointed star formed by two equally annularly displaced delta triangles.

13. A medical device as defined in claim 12 wherein the fixed association of each fixed flexure element with a movable flexure element constitutes a connection comprising a heat shrunk tube in surrounding relation to the distal end of the associated fixed flexure element with an annular layer of fused adhesive plastic between the heat shrunk tube and the distal end of the associated fixed flexure element and the distal end of the associated movable flexure element being in contact with the fixed flexure element and the annular layer of fused adhesive plastic.

14. A medical device as defined in claim 9 wherein the fixed association of each fixed flexure element with a movable flexure element constitutes a connection comprising a heat shrunk tube in surrounding relation to the distal end of the associated fixed flexure element with an annular layer of fused adhesive plastic between the heat shrunk tube and the distal end of the associated fixed flexure element and the distal end of the associated movable flexure element being in contact with the fixed flexure element and the annular layer of fused adhesive plastic.

\* \* \* \* \*